(12) United States Patent
Wang et al.

(10) Patent No.: US 12,167,953 B2
(45) Date of Patent: Dec. 17, 2024

(54) ANIMAL IRRADIATION SYSTEM

(71) Applicant: NEUBORON MEDTECH LTD., Jiangsu (CN)

(72) Inventors: Dong-chun Wang, Jiangsu (CN); Yuan-hao Liu, Jiangsu (CN); Hong-feng Ji, Jiangsu (CN); Fa-zhi Yan, Jiangsu (CN)

(73) Assignee: NEUBORON MEDTECH LTD., Nanjing (CN)

( * ) Notice: Subject to any disclaimer, the term of this patent is extended or adjusted under 35 U.S.C. 154(b) by 89 days.

(21) Appl. No.: 17/974,648

(22) Filed: Oct. 27, 2022

(65) Prior Publication Data

US 2023/0057879 A1    Feb. 23, 2023

Related U.S. Application Data

(63) Continuation of application No. PCT/CN2021/128841, filed on Nov. 5, 2021.

(30) Foreign Application Priority Data

Nov. 23, 2020 (CN) .......................... 202011322578.0

(51) Int. Cl.
*A61N 5/10* (2006.01)
*A61D 3/00* (2006.01)

(52) U.S. Cl.
CPC ............. *A61D 3/00* (2013.01); *A61N 5/1077* (2013.01); *A61N 2005/109* (2013.01); *A61N 2005/1092* (2013.01); *A61N 2005/1097* (2013.01)

(58) Field of Classification Search
None
See application file for complete search history.

(56) References Cited

U.S. PATENT DOCUMENTS

| | | |
|---|---|---|
| 5,320,069 A | 6/1994 | Anderson, Jr. et al. |
| 2014/0270076 A1 | 9/2014 | Pelloski et al. |

(Continued)

FOREIGN PATENT DOCUMENTS

| | | |
|---|---|---|
| CN | 101167667 A | 4/2008 |
| CN | 201977959 U | 9/2011 |

(Continued)

OTHER PUBLICATIONS

International Search Report of PCT/CN2021/128841, Jan. 26, 2022.

*Primary Examiner* — Eliza W Osenbaugh-Stewart
(74) *Attorney, Agent, or Firm* — Locke Lord LLP; Tim Tingkang Xia, Esq.

(57) ABSTRACT

An animal irradiation system includes a radioactive source and an irradiation fixing apparatus having irradiated bodies. The radioactive source includes a beam outlet having a first central axis. Radioactive rays generated by the radioactive source exit from the beam outlet and irradiate the irradiated bodies. The radioactive rays define a main axis around the first central axis. The irradiation fixing apparatus includes a box body, which is divided into multiple accommodating chambers around a second central axis. Each accommodating chamber accommodates an irradiated body. Multiple first irradiation holes corresponding to the accommodating chambers are formed on the box body. The radioactive rays pass through the first irradiation holes and then irradiate the irradiated bodies. A maximum distance from an inner wall of each first irradiation hole to the first central axis is less than a minimum distance from an inner wall of the beam outlet to the first central axis.

16 Claims, 3 Drawing Sheets

(56) References Cited

U.S. PATENT DOCUMENTS

2019/0105512 A1\* 4/2019 Liu .................... A61N 5/1081
2019/0224499 A1 7/2019 Liu

FOREIGN PATENT DOCUMENTS

| CN | 103565537 | A | 2/2014 |
| CN | 103598926 | A | 2/2014 |
| CN | 204325372 | U | 5/2015 |
| CN | 206167657 | U | 5/2017 |
| CN | 208355944 | U | 1/2019 |
| CN | 110522531 | A | 12/2019 |
| CN | 111686376 | A | 9/2020 |
| CN | 214435888 | U | 10/2021 |
| JP | H0531131 | A | 2/1993 |
| JP | 2017173283 | A | 9/2017 |
| JP | 2019037697 | A | 3/2019 |

\* cited by examiner

ANIMAL IRRADIATION SYSTEM

CROSS-REFERENCE TO RELATED PATENT APPLICATION

This application is a continuation application of International Application No. PCT/CN2021/128841, filed on Nov. 5, 2021, which claims priority to Chinese Patent Application No. 202011322578.0, filed on Nov. 23, 2020, the disclosures of which are hereby incorporated by reference.

FIELD

The present disclosure relates to a radioactive ray irradiation system, and, more particular, to an animal irradiation system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

With the development of atomic science, radioactive ray therapy, such as cobalt 60, linear accelerator, electron beam and the like, has become one of the main means of cancer treatment. However, traditional photon or electron therapy is limited by the physical conditions of radioactive ray itself, which not only kills tumor cells, but also damages a large number of normal tissues on the beam path. In addition, due to the different sensitivities of tumor cells to radioactive rays, traditional radiotherapy is often in effective in treatment of radiation-resistant malignant tumors (such as glioblastoma multiforme and melanoma).

In order to reduce the radioactive ray injury of normal tissues around tumors, the concept of target therapy in chemotherapy has been applied to radiotherapy. For tumor cells with high radioactive ray resistance, radioactive sources with high relative biological effectiveness (RBE) are also actively developed, such as proton therapy, heavy particle therapy, neutron capture therapy and the like. Neutron capture therapy combines the above two concepts, such as boron neutron capture therapy, which provides a better option of cancer treatment than traditional radioactive rays via a boron-containing drug specifically accumulated in tumor cells and in combination with precise neutron beam regulation.

Figure 1:
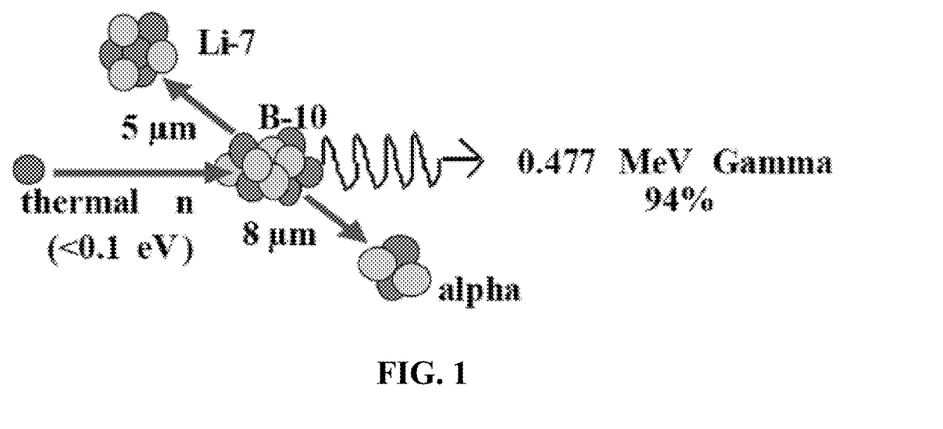
FIG. 1 is a scheme diagram of boron neutron capture reaction.
Figure 2:
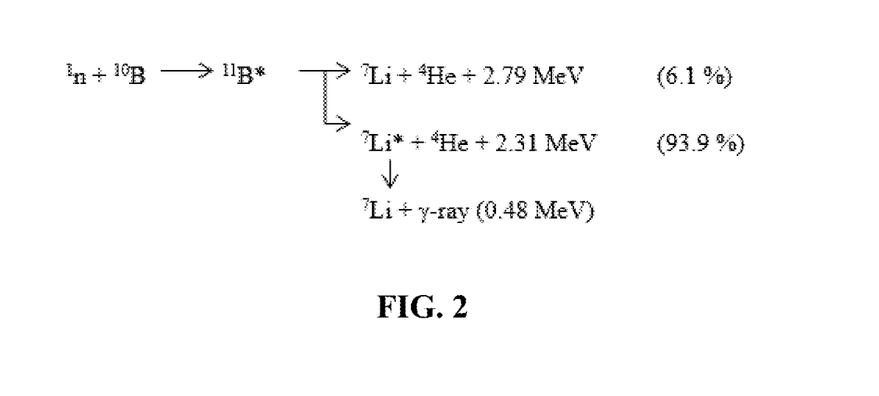
FIG. 2 is $^{10}B$ $(n, \alpha)^{7}Li$ neutron capture nuclear reaction equation.

The boron neutron capture therapy (BNCT) utilizes the property of the boron ($^{10}B$)-containing drug that has a high cross-section for capturing thermal neutrons, by $^{10}B$ (n, α)$^7$Li neutron capture and nuclear fission reaction, generating two heavily charged particles $^4$He and $^7$Li. Referring to FIGS. 1 and 2, a scheme diagram of the boron neutron capture reaction and $^{10}B$ (n, α)$^7$Li neutron capture nuclear reaction equation are shown, respectively. An average energy of the two charged particles is about 2.33 MeV, which has the characteristics of high linear energy transfer (LET) and short range. The linear energy transfer and the range of the α particle is 150 keV/μm and 8 μm, respectively; while the linear energy transfer and the range of the $^7$Li heavy particle is 175 keV/μm, and 5 μm. The total range of two particles is approximately equivalent to the size of a cell, so the radioactive ray damage to organisms can be limited to the cell level. When boron-containing drugs are selectively gathered in tumor cells, with appropriate neutron sources, the purpose of killing tumor cells locally can be achieved without causing too much damage to normal tissues.

In order to study the biological effects of radioactive rays and verify the effect of radiotherapy, it is necessary to carry out animal irradiation experiments before clinical treatment. In the experiments, it is usually necessary to fix and irradiate several animals in the same group at the same time to carry out related irradiation researches.

SUMMARY

To solve the above problems, one aspect of the present disclosure provides an irradiation fixing apparatus for an animal irradiation system. The animal irradiation system comprises a radioactive source. The radioactive source comprises a beam outlet. The radioactive rays generated by the radioactive source are irradiated from the beam outlet to a plurality of irradiated bodies in the irradiation fixing apparatus. The radioactive rays from the beam outlet are around a first central axis to define a main axis. The irradiation fixing apparatus comprises a box body for accommodating the irradiated bodies. The box body is provided with a second central axis. The box body is circumferentially separated into a plurality of accommodating chambers around the second central axis. Each of the accommodating chambers is configured to accommodate a corresponding irradiated body. A plurality of first irradiation holes, each corresponding to one of the accommodating chambers, are arranged on the box body. The radioactive rays generated by the radioactive source irradiate the corresponding irradiated body in each of the accommodating chambers through a corresponding one of the first irradiation holes. A maximum distance from inner walls of the first irradiation holes to the first central axis are smaller than a minimum distance from an inner wall of the beam outlet to the first central axis. Therefore, all the first irradiation holes are located in the irradiation range of the radioactive source, and a plurality of the irradiated bodies can be irradiated simultaneously, thus improving the experimental efficiency.

Preferably, the second central axis and the first central axis coincide, or are parallel to each other or inclined to each other.

Preferably, the second central axis coincides with the first central axis. A plurality of the accommodating chambers are uniformly distributed circumferentially around the second central axis, the multiple first irradiation holes have the same arrangement, and the distances from multiple first irradiation holes to the second central axis are equal. Therefore, all the irradiated bodies in the irradiation fixing apparatus undergoing a comparative experiment obtain the same dose of irradiation.

Preferably, each of the first irradiation holes has a third central axis, and a distance between the inner wall of the first irradiation hole and the third central axis gradually decreases along a direction of the direction of the radioactive rays. In such way, the neutron beam is focused on the part to be irradiated of the irradiated bodies. Further, the third central axes are parallel to the second central axis.

Preferably, the box body comprises a base and a cover plate, the base comprises a bottom plate and separators, wherein the separators are a plurality of protruding parts extending from the bottom plate or the cover plate along a direction parallel to the second central axis and distributed circumferentially around the second central axis, and the box body is circumferentially divided into a plurality of the accommodating chambers by the separators around the second central axis. Further, the first irradiation holes are circumferentially distributed around the second central axis and provided on one of the bottom plate and the cover plate, and the first irradiation holes extend through in a direction parallel to the second central axis to communicate with each of the accommodating chambers. Furthermore, the other one of the bottom plate and the cover plate is provided with vent holes penetrating in directions parallel to the second central axis, which is convenient for the irradiated bodies to breathe and carry out irradiation experiments on the living body or under anesthesia.

Preferably, the irradiation fixing apparatus further comprises an irradiated body fixing part, which is detachably installed in one accommodating chamber and positioned relative to the accommodating chamber. Further, the irradiated body fixing part is a fixing tube, which comprises a tube body for accommodating their radiated body and a fixing means for fixing the irradiated bodies in the tube body, a second irradiation hole is provided in the tube body, and the radioactive rays generated by the radioactive source irradiate the irradiated bodies through the first and second irradiation holes. The position of each irradiated body in their radiation fixing apparatus is defined by the fixing tube. Each irradiated body is more convenient and fast to be positioned, and each irradiated body does not need anesthesia, and therefore more accurate experimental data can be obtained. Further, each of the fixing means comprises a fixing sleeve and a locking means provided in the tube body, the fixing sleeve is configured to fix a preset part of each irradiated body, the fixing sleeve is able to move in the tube body and is fixed through the locking means.

Preferably, a material of the irradiation fixing apparatus is organic glass, which has certain strength and generates radioisotopes with a short half-life after activated by neutrons, thus reducing the dose of radioactive rays to non-irradiated part of each irradiated body. In another preferable embodiment, the material of the irradiation fixing apparatus is transparent to facilitate observation of the state of each irradiated body. In yet another preferable embodiment, the irradiation fixing apparatus is made into a hollow structure, and the hollow structure is filled with a material that can shield neutrons or photons, such as lithium carbonate, lithium fluoride or boron-containing compounds, so as to minimize the non-selective dose deposition of normal tissues and reduce the dose of radioactive rays to the non-irradiated part of each irradiated body, thus the experimental results will be more accurate.

Another aspect of the present disclosure provides an animal irradiation system, comprising a radioactive source and an irradiation fixing apparatus, in which the irradiation fixing apparatus is fixed with respect to the radioactive source, the radioactive source is configured to generate radioactive rays and irradiate a plurality of irradiated bodies in the irradiation fixing apparatus.

Further, the radioactive source comprises a neutron generating device for generating a neutron beam and forming a beam outlet, from which the neutron beam generated by the neutron generating device irradiates toward the irradiated body in the irradiation fixing apparatus, and the irradiation fixing apparatus are detachably connected to the beam outlet.

Preferably, the radioactive source also comprises a beam shaper or a collimator. The beam shaper is configured to adjust beam quality of the neutron beam, the collimator is configured to converge the neutron beam, the neutron beam generated by the neutron generating device is irradiated to the irradiated bodies in the irradiation fixing apparatus through the beam shaper or the collimator, the beam shaper or the collimator forms the beam outlet, and the irradiation fixing apparatus is detachably connected to the beam shaper or the collimator.

Preferably, the neutron generating device comprises an accelerator and a target. The accelerator is configured to accelerate protons and generate a proton line, and the proton line irradiates the target and interacts with the target to generate neutrons.

The animal irradiation system and the irradiation fixing apparatus described in disclosure can fix and irradiate a plurality of irradiated bodies at the same time, thus improving the experimental efficiency.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

The embodiments of the present disclosure are further described in detail below with reference to the accompanying drawings, so that those skilled in the art can implement the technical solutions according to the description.

Figure 3:
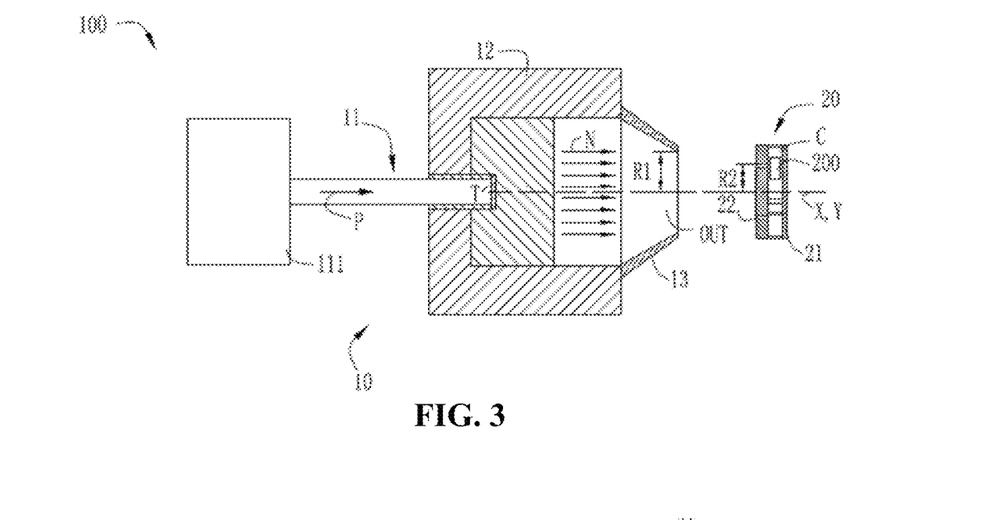
FIG. 3 is a scheme diagram of an animal irradiation system in an embodiment of the disclosure.

As shown in FIG. 3, an animal irradiation system 100 comprises a radioactive source 10 and an irradiation fixing apparatus 20. The radioactive source 10 is configured to generate radioactive rays and comprises a beam outlet OUT, and the irradiation fixing apparatus 20 is configured to accommodate an irradiated body 200. Specifically, FIG. 3 shows only one irradiated body 200 being accommodated in the irradiation fixing apparatus 20, but it is possible that the irradiation fixing apparatus 20 may accommodate a plurality of irradiated bodies. During irradiating, the irradiated body 200 is first positioned in the irradiation fixing apparatus 20, and then the irradiation fixing apparatus 20 is fixed relative to the radioactive source 10. Then the radioactive source 10 is controlled to generate radiation, which emits from the beam outlet OUT and irradiates the irradiated body 200 (or multiple irradiated bodies 200) in the irradiation fixing apparatus 20.

In this embodiment, the animal irradiation system 100 is a boron neutron capture therapy system, and the radioactive source 10 comprises a neutron generating device 11, a beam shaper 12 and a collimator 13. The neutron generating device 11 is configured to generate a neutron beam N, and the neutron generating device 11 comprises an accelerator 111 and a target T. The accelerator 111 accelerates charged particles (such as protons, deuterons, etc.) to generate charged particle line P such as proton line. The charged particle line P irradiates the target T and interacts with the target T to generate neutrons, and the neutrons form a neutron beam N. An appropriate nuclear reaction can be selected according to required neutron yield and energy, available energy and current of the accelerated charged particles, and physicochemical properties of the target. Specific structures of the accelerator and the target are not described in detail here. The beam shaper 12 is configured to adjust the beam quality of the neutron beam N, and the collimator 13 is configured to concentrate the neutron beam N, so that the neutron beam N has higher targeting in a treatment process. The collimator 13 forms a beam outlet OUT, and the neutron beam N around a central axis X coming out of the beam outlet OUT defines a main axis. The neutron beam N generated by the neutron generating device 11 passes the beam shaper 12 and the collimator 13 sequentially, and irradiates to the irradiated body 200 (or multiple irradiated bodies 200) in the irradiation fixing apparatus 20. The direction of the neutron beam N shown in the figures and described below does not represent an actual direction of neutron movement, but rather represents a direction of an overall movement trend of the neutron beam N. It is to be understood that the neutron generating device 11 may also have other structures, for example, it may use a neutron source other than an accelerator. Structures of the beam shaper 12 and the collimator 13 are not described in detail here. It is to be understood that the radioactive source 10 can also be used for treatment of tumor patients after animal irradiation experiments. The radioactive source may also have other structures, for example, it may have other radioactive ray generating device, or may not have a beam shaper or a collimator, or the neutron generating device 11 or the beam shaper 12 may also form a beam outlet OUT.

Figure 4:
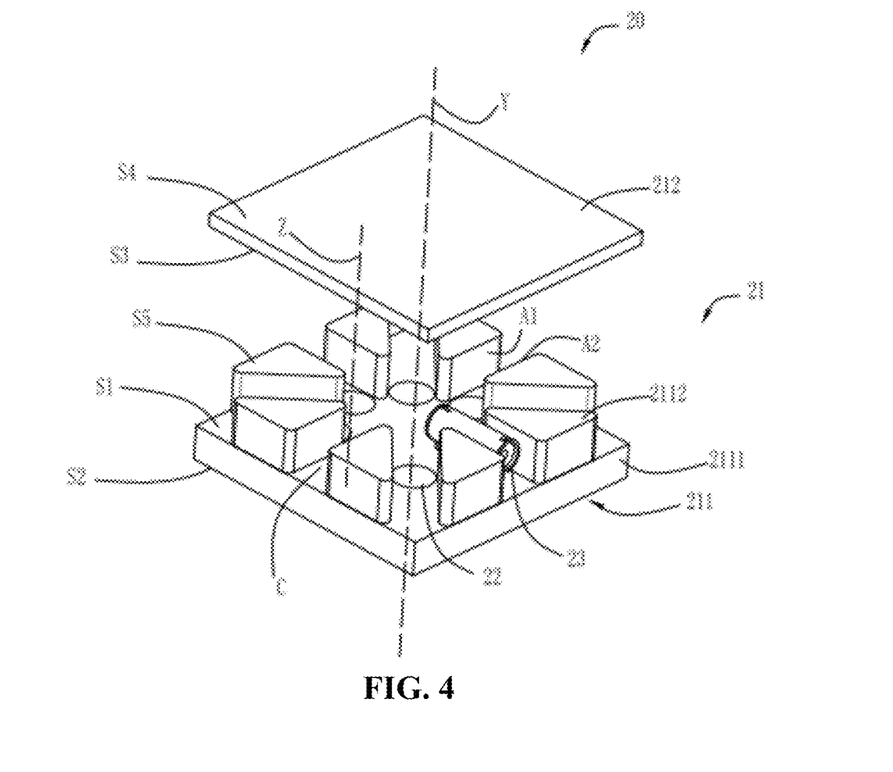
FIG. 4 is an exploded scheme diagram of a structure of the irradiation fixing apparatus in the animal irradiation system of FIG. 3.

The irradiation fixing apparatus 20 comprises a box body 21 containing the irradiated body 200 (or multiple irradiated bodies 200). The box body 21 has a central axis Y. The box body 21 is circumferentially divided into multiple accommodation chambers C around the central axis Y. Each accommodation chamber C is configured to accommodate an irradiated body 200 (such as a mouse, it is to be understood that other animals suitable for irradiation experiments can also be selected). During irradiation, a corresponding accommodation chamber C can be selected to accommodate an irradiated body 200 according to needs, and only one irradiated body 200 is schematically illustrated in the figure. Multiple first irradiation holes 22 corresponding to each accommodating chamber C are provided on the box body 21. Radioactive rays from the radioactive source 10 irradiate the irradiated body in the accommodating chamber C through the first irradiation holes 22. The maximum distance R1 from the inner walls of the first irradiation holes 22 to the central axis X are smaller than the minimum distance R2 from the inner wall of the beam outlet OUT to the central axis X, that is, all the first irradiation holes 22 are located within a irradiation range of the radioactive source 10. The irradiation fixing apparatus 20 of the present disclosure can simultaneously fix and irradiate multiple irradiated bodies, thereby improving experimental efficiency. In this embodiment, after the irradiation fixing apparatus 20 is fixed with respect to the radioactive source 10, the central axis Y coincides with the central axis X of the beam outlet OUT. The multiple accommodating chambers C are uniformly distributed circumferentially around the central axis Y. The multiple first irradiation holes 22 have the same arrangement and the same distance from the central axis Y, that is, the distances between the first irradiation holes 22 and the central axis X are the same, so that all the irradiated bodies in the irradiation fixing apparatus 20 obtain the same dose of radiation. It is to be understood that there may be other settings according to different experimental requirements. For example, the central axis Y and the central axis X may be parallel to each other or inclined. In this embodiment, each first irradiation hole 22 has a central axis Z (as shown in FIG. 4), and the first irradiation hole 22 extends tapered around the central axis Z, that is, the radial distance of the inner wall of the first irradiation hole 22 from the central axis Z of the first irradiation hole 22 in the direction of the neutron beam N is gradually reduced, so as to focus the neutron beam on the part to be irradiated of the irradiated body. The first irradiation holes 22 extend in a direction parallel to the central axis Y, that is, the central axis Z is parallel to the central axis Y. It is to be understood that there may be other arrangements.

Referring to FIG. 4 the box body 21 of the irradiation fixing apparatus 20 comprises a base 211 and a cover plate 212. The base 211 further comprises a bottom plate 2111 and separators 2112. The bottom plate 2111 and the cover plate 212 have same central axes as the central axis Y of the box body 21. The separators 2112 are multiple projections extending from the bottom plate 2111 in directions parallel to the central axis Y and distributed circumferentially around the central axis Y. The box body 21 is divided into the multiple accommodating chambers C circumferentially around the central axis Y by the separators 2112. The first irradiation holes 22 are provided on the bottom plate 2111 circumferentially distributed around the central axis Y, and extend through the bottom plate 2111 in directions parallel to the central axis Y so as to communicate with each of the accommodating chambers C. In this embodiment, the bottom plate 2111 and the cover plate 212 are flat plates. The bottom plate 2111 has a first plate surface S1 facing the cover plate 212 and a second plate surface S2 facing away from the cover plate 212. The cover plate 212 has a third plate surface S3 facing the bottom plate 2111 and a fourth plate surface S4 facing away from the bottom plate 2111. The first, second, third, and fourth plate surfaces S1-S4 are parallel to each other and perpendicular to the central axis Y of the box body 21, that is, the neutron beam N is incident perpendicular to the plate surface. The separators 2112 extend from the first plate surface S1 of the bottom plate 2111 and each has a fifth plate surface S5 perpendicular to the central axis Y of the box body 21. It is to be understood that other arrangement may also be possible. In the embodiment, the numbers of the separator 2112, the accommodating chambers C, and the first irradiation holes 22 are eight and are uniformly distributed circumferentially around the central axis Y. It is to be understood that other arrangement may also be possible. The separators 2112 and the bottom plate 2111 may be integrated or fixedly connected by means of bonding or the like. After the irradiated bodies are installed in the accommodating chambers C and positioned, the cover plate 212 and the base 211 are fixed by such as a screw connection, bonding, or the like, which is not particularly limited. The fifth plate surfaces S5 of the separators 2112 contact the third plate surface S3 of the cover plate 212 for positioning. The cover plate 212 may also be provided with vent holes (not shown) penetrating along the central axis Y direction. Shape, position, number, etc. of the vent holes are not specifically limited. For example, the vent holes are provided at positions corresponding to the accommodating chambers C, so that the irradiated bodies can breathe conveniently and irradiation experiments can be performed on living bodies or under anesthesia.

It is to be understood that the positions of the first irradiation holes 22 and the vent holes can be interchanged, such as the first irradiation holes 22 are provided at positions corresponding to the accommodating chambers C on the cover plate 212, and the vent holes are provided at positions corresponding to the accommodating chambers C on the bottom plate 2111. The outer contours of the bottom plate 2111 and the cover plate 212 in the direction perpendicular to the central axis Y may be made into any one of a rectangle, a square, and a circle as required, and it is a square in the embodiment. The outer contour of the separator 2112 in the direction perpendicular to the central axis Y is approximately triangular, and two adjacent ones of the separators 2112 have side walls A1 and A2 parallel to each other to form an accommodating chamber C. It is to be understood that other structures may also be provided, for example, the separators 2112 may be provided on the bottom plate 2111 and the cover plate 212 at the same time, and a cross section of an accommodating chamber C is circular, or the like. A cross section of a first irradiation hole 22 in the direction perpendicular to the central axis Y is circular, and it is to be understood that other shapes may also be taken. It is to be understood that the box body 21 may have other structures which are not specifically limited by the present disclosure.

After the part to be irradiated (e.g. tumor tissue of a mouse) of an irradiated body 200 is aligned with a first irradiation hole 22, the irradiated body 200 can be directly fixed in the accommodating chamber C by an adhesive tape or the like, or the irradiated body 200 is positioned and installed in the accommodating chamber C by an irradiated body fixing part. For example, the irradiated body 200 is tied to the irradiated body fixing part, which is detachably installed in the accommodating chamber C and positioned relative to the accommodating chamber C (for example, by a positioning pin). In the embodiment, the irradiation fixing apparatus 20 further comprises a fixing tube 23 for positioning an irradiated body 200 and aligning the part to be irradiated with the first irradiation hole 22. Meanwhile, the fixing tube 23 is detachably installed in an accommodating chamber C, and thus an irradiated body 200 can be independently positioned outside the box body 21; and after positioning, the fixing tube 23 containing the irradiated body 200 is installed in the box body 21. One fixing tube 23 can be provided in each of the accommodating chambers C, and only one fixing tube is schematically shown in FIG. 4. In use according to specific requirements, one or more accommodating chambers C may be installed with fixing tube(s) 23 and the irradiated bodies 200 to be irradiated may be arranged in the fixing tubes 23.

Figure 5:
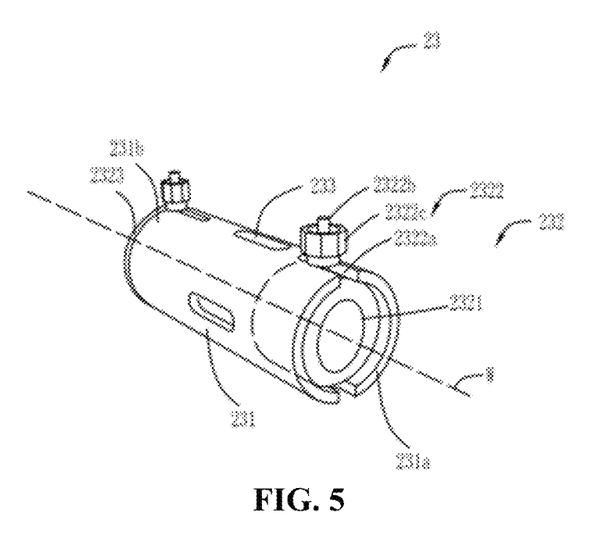
FIG. 5 is a scheme diagram of a structure of a fixing tube in the irradiation fixing apparatus of FIG. 4.

Referring to FIG. 5, the fixing tube 23 comprises a tube body 231 accommodating an irradiated body 200 and a fixing means 232 fixing the irradiated body within the tube body 231. The tube body 231 is provided with a second irradiation hole 233. The position of the irradiated body 200 is such defined by the fixing means 232 that the part to be irradiated corresponds to the second irradiation hole 233. After the fixing tube 23 is installed in an accommodating chamber C, the second irradiation hole 233 corresponds to a first irradiation hole 22, and radioactive rays generated by the radioactive source 10 irradiate the irradiated body 200 through the first and second irradiation holes 22 and 233, that is, the neutron beam N can be directly irradiated to the part to be irradiated of the irradiated body 200.

The fixing means 232 comprises a fixing sleeve 2321 and a locking means 2322. The fixing sleeve 2321 is configured to fix a preset part of the irradiated body 200. The fixing sleeve 2321 can be moved in the tube body 231 and fixed by the locking means 2322 to a desired position, that is the position where the part to be irradiated corresponds to the second irradiation hole 233. In the embodiment, the fixing sleeve 2321 is configured to fix the head of a mouse. The fixing sleeve 2321 has an inner diameter smaller than an outer diameter of a mouse head, thereby preventing the mouse from passing through and restricting movement of the mouse, or clamping at least part of the mouse head within the inner diameter of the fixing sleeve 2321. In the embodiment, the locking means 2322 comprises a sliding groove 2322a provided on the pipe wall of the tube body 231, a threaded rod 2322b which passes through the sliding groove 2322a and is fixedly connected to the fixing sleeve 2321, and a nut 2322c which is provided outside the tube body 231 and is screwed to the threaded rod 2322b. By rotating the nut 2322c, the fixing sleeve 2321 is fixed to the tube body 231 after the nut is tightened; and the fixing sleeve 2321 is capable of sliding along the sliding groove 2322a in the tube body 231 by holding the nut 2322c after the nut is loosened. In the embodiment, the sliding groove 2322a extends from one end 231a of the tube body 231, that is, the sliding groove 2322a is opened at one end and has a U-shape. The fixing sleeve 2321 can slide out of the tube body 231 along the sliding groove 2322a, thus the irradiated body 200 can be conveniently fixed relative to the fixing sleeve 2321. It is to be understood that the sliding groove 2322a may not have an opening, so it is necessary to directly put the irradiated body 200 into the tube body 231 and fix the irradiated body 200 through the fixing sleeve 2321. It is to be understood that the fixing means may have other arrangement, such as providing a threaded hole in the fixing sleeve 2321 and the threaded rod connected to the threaded hole passing through the sliding groove 2322a. An end plate 2323 may be provided at the other end 231b of the tube body 231, and may be locked with the fixing sleeve 2321 in the same manner, so as to close the tube body 231 relatively and prevent the irradiated body 200 from escaping. An opening may also be provided on the end plate 2323, and the tail of a mouse can pass through the opening, which provides convenience for tail intravenous injection and blood drawing. The end plate 2323 may also be replaced by a second fixing sleeve, which may be adjusted according to the length of the irradiated body 200 to better limit the movement of the irradiated body and avoid interference to the experiment due to the movement of the animal.

In the embodiment, the tube body 231 has a central axis W, which is perpendicular to the central axis Y of the box body 21 after the fixing tube 23 is installed to an accommodating chamber C. The cross section of the tube body 231 perpendicular to the central axis W may be a ring or other shape. The tube body 231 may also be provided with a vent hole (not shown), and the shape, position, number, etc. of the vent hole(s) are not specifically limited. The number of second irradiation holes 233 may be plural, which is more convenient, since the part to be irradiated of the irradiated body 200 may correspond to any one of the second irradiation holes 233. The second irradiation holes 233, through which no radioactive ray passes during irradiation, may also serve as vent holes. It is to be understood that the fixing tube 23 may also have other structures. According to the present disclosure, the irradiated body 200 is limited in the irradiation fixing apparatus 20 by using the fixing tube 23, so that the irradiated body 200 can be positioned more conveniently and quickly, and at the same time, the irradiated body 200 does not need anesthesia, so that more accurate experimental data can be obtained.

A neutron source of boron neutron capture therapy generates mixed radiation field, that is, a beam contains neutrons and photons with low energy to high energy. For boron neutron capture therapy of deep tumors, the more radioactive rays other than epithermal neutrons, the greater the proportion of non-selective dose deposition in normal tissues, so the radioactive rays that may cause unnecessary dose should be reduced as much as possible. In an embodiment, the irradiation fixing apparatus 20 is made of organic glass, for example, the bottom plate 2111, the separators 2112 and the cover plate 212 of the box body 21, as well as the tube body 231, the fixed sleeve 2322 and the end plate 2323 of the fixing tube 23, and the like are made of organic glass. Organic glass has certain strength and generates radioisotopes with a short half-life after being activated by neutrons, which reduces the radiation dose to non-irradiated parts of the irradiated body. It is to be understood that the irradiation fixing apparatus 20 may be made of other materials which can shield neutrons or photons. The material of the irradiation fixing apparatus 40 may also be transparent to facilitate observation of state of the irradiated body. The material of the irradiation fixing apparatus 20 may also be made into a hollow structure, which may be filled with materials that can shield neutrons or photons, such as lithium carbonate, lithium fluoride or boron-containing compounds, so as to minimize the non-selective dose deposition of normal tissues and reduce the radiation dose to the non-irradiated parts of the irradiated body, thus making the experimental results more accurate.

After the irradiated body 200 is limited in the fixing tube 23, the fixing tube 23 is installed in the accommodating chamber C. The fixing tube 23 can be fixed in the accommodating chamber C in a variety of ways, such as bonding, inserting, hook connection, screw connection, and the like. In an embodiment, the fixing tube 23 is fixed in the accommodating chamber C by fixing its position with a groove. For example, an L-shaped groove is formed in the bottom plate 2111. The width of the groove is just wide enough to accommodate the nut 2322c on the fixing tube 23. The fixing tube 23 is placed in the accommodating chamber C, the nut 2322C slides in along one side of the L-shaped groove, and then rotates along the other side, and then the position of the fixing tube 23 is axially fixed along the direction of the central axis W, so that a biasing force can be applied circumferentially around the central axis W by a spring or the like.

It is to be understood, a cylinder may be provided at the center of the first plate surface S1 of the bottom plate 2111. The height of the cylinder in a direction parallel to the central axis Y (a distance to the first plate surface S1) is less than or equal to the height of the fifth plate surface S5 of the separator 2112 in a direction parallel to the central axis Y (a distance to the first plate surface S1). A screw passes through the center of the cover plate 212 and is screwed with the cylinder, so that the base 211 and the cover plate 212 are fixed together. The cylinder can also assist in limiting the position of the irradiated body 200 or the fixing tube 23. The irradiation fixing apparatus 20 in the embodiment has a simple structure convenient to be installed, and can simultaneously fix multiple irradiated bodies 200 for irradiation. It is to be understood that the irradiation fixing apparatus 20 may have other structures.

Finally, the irradiation fixing apparatus 20 installed with irradiated bodies 200 is fixed with respect to the radioactive source 10 in a variety of ways, such as bonding, inserting, hook connection, screw connection, etc. In the embodiment, the irradiation fixing apparatus 20 is detachably connected to the collimator 13 (FIG. 3 only shows a state where the irradiation fixing apparatus 20 and the collimator 13 are not connected), thus the irradiation fixing apparatus is easy to be disassembled and replaced. For example, the second plate surface S2 of the bottom plate 2111 is connected to the end of the collimator 13 in a direction facing the neutron beam N. It is to be understood that the irradiation fixing apparatus 20 may also be fixed to other sites of the radioactive source 10. Alternatively, it may not be directly fixed to the radioactive source 10, for example, it may be fixed to a corresponding position on the ground or a wall.

The following is a description of an irradiation experiment process of boron neutron capture therapy on irradiated bodies (taking mice as an example) in combination with the embodiments of the present disclosure.

First, a mouse is injected with a boron-containing drug and placed into a fixing tube 23. The nut 2322c on the fixing tube 23 is loosened, and the fixing sleeve 2321 is slid out of the tube body 231 along the sliding groove 2322a by holding the nut 2322c. The mouse head is fixed in the fixing sleeve 2321, ensuring the part to be irradiated to be on a side corresponding to a second irradiation hole 233. The mouse and the fixing sleeve 2321 are loaded into the tube body 231, a sliding position of the fixing sleeve 2321 is adjusted by holding the nut 2322C to ensure that the part to be irradiated coincides with the second irradiation hole 233, and then the position of the fixing sleeve 2321 is fixed by tightening the nut 2322C. An end plate 2323 is installed and fixed, and the tail of the mouse is taken out from the opening 2323a of the end plate 2323. If the mouse is too small, filler can be added between the end plate 2323 and the mouse.

Then, the fixing tube 23 containing the mouse is placed in one accommodating chamber C for positioning. At this time, the part to be irradiated of the mouse corresponds to the first irradiation hole 22 and second irradiation hole 233, and the cover plate 212 is fixedly connected to the base 211.

Finally, the irradiation fixing apparatus 20 is fixed to the collimator 13, so that the first irradiation hole 22 faces the beam outlet OUT, and the central axis Y coincides with the central axis X. A neutron beam N is generated by nuclear reaction between a proton beam (with energy ranging from 1.881 MeV to 30 MeV) and target T, passes through the beam shaper 12 and the collimator 13 and comes from beam outlet OUT, and then irradiates to the tumor tissue of the mouse in irradiation fixing apparatus 20 through the first and second irradiation holes 22 and 233 to perform the boron neutron capture therapy.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:
1. An animal irradiation system comprising:
a radioactive source and an irradiation fixing apparatus;
wherein the radioactive source comprises:

a beam outlet, from which radioactive rays generated by the radioactive source are irradiated to a plurality of irradiated bodies in the irradiation fixing apparatus, and wherein the irradiation fixing apparatus comprises:

a box body configured to accommodate the irradiated bodies, wherein the box body is divided into a plurality of accommodating chambers, each of the plurality of accommodating chambers is configured to accommodate a corresponding one of the irradiated bodies, the irradiation fixing apparatus further comprises an irradiated body fixing part, the irradiated body fixing part is detachably installed in one of the accommodating chambers and positioned relative to the corresponding accommodating chamber, wherein the irradiated body fixing part is a fixing tube comprising a tube body and a fixing means, wherein the tube body is provided to accommodate the irradiated body, and the fixing means is provided to fix the irradiated body in the tube body.

2. The animal irradiation system according to claim 1, wherein the beam outlet comprises a first central axis and defines a main axis around the first central axis, wherein the irradiation fixing apparatus further comprises a plurality of first irradiation holes arranged on the box body, wherein the box body has a second central axis and is circumferentially separated into a plurality of accommodating chambers around the second central axis, each of the accommodating chambers is configured to accommodate the corresponding one of the irradiated bodies, each of the plurality of first irradiation holes is corresponding to one of the accommodating chambers, the radioactive rays generated by the radioactive source irradiate the corresponding one of the irradiated bodies in each of the accommodating chambers through a corresponding one of the first irradiation holes, and a maximum distance from inner walls of the first irradiation holes to the first central axis is smaller than a minimum distance from an inner wall of the beam outlet to the first central axis.

3. The animal irradiation system according to claim 2, wherein a second irradiation hole is provided in the tube body, and the radioactive rays generated by the radioactive source irradiates the irradiated bodies through the first and second irradiation holes.

4. The animal irradiation system according to claim 3, wherein the fixing means comprises a fixing sleeve and a locking means provided in the tube body, the fixing sleeve is configured to fix a preset part of the irradiated bodies, the fixing sleeve is able to move in the tube body and is fixed by the locking means.

5. The animal irradiation system according to claim 2, wherein the second central axis coincides with the first central axis, a plurality of the accommodating chambers are uniformly distributed circumferentially around the second central axis, the first irradiation holes have a same arrangement with the accommodating chambers, and the distances from the plurality of the first irradiation holes to the second central axis are equal.

6. The animal irradiation system according to claim 2, wherein each of the first irradiation holes has a third central axis, and a distance between the inner wall of the first irradiation hole and the third central axis gradually decreases along a direction of the radioactive rays.

7. The animal irradiation system according to claim 6, wherein the third central axis is parallel to the second central axis.

8. The animal irradiation system according to claim 1, wherein the irradiation fixing apparatus is made of organic glass material or transparent material or with a hollow structure, wherein the hollow structure is filled with neutron shielding material or photon shielding material.

9. The animal irradiation system according to claim 1, wherein the irradiation fixing apparatus is fixed with respect to the radioactive source.

10. The animal irradiation system according to claim 1, wherein the radioactive source comprises:

a neutron generating device configured to generate a neutron beam and form the beam outlet, the neutron beam coming out of the beam outlet irradiates the irradiated bodies in the irradiation fixing apparatus; and an irradiation fixing apparatus detachably connected to the beam outlet.

11. The animal irradiation system according to claim 10, wherein the radioactive source also comprises a beam shaper or a collimator, wherein the beam shaper is configured to adjust beam quality of the neutron beam, the collimator is configured to converge the neutron beam, the neutron beam generated by the neutron generating device is irradiated to the irradiated bodies in the irradiation fixing apparatus through the beam shaper or the collimator, the beam shaper or the collimator forms the beam outlet, and the irradiation fixing apparatus is detachably connected to the beam shaper or the collimator.

12. The animal irradiation system according to claim 10, wherein the neutron generating device comprises an accelerator and a target, wherein the accelerator is configured to accelerate protons and generate a proton line, and the proton line irradiates the target and interacts with the target to generate neutrons.

13. The animal irradiation system according to claim 10, wherein the beam outlet comprises a first central axis and defines a main axis around the first central axis, the irradiation fixing apparatus comprises a box body configured to accommodate the irradiated bodies and a plurality of first irradiation holes arranged on the box body, wherein the box body comprises a second central axis and is circumferentially separated into a plurality of accommodating chambers around the second central axis, each of the accommodating chambers is configured to accommodate a corresponding one of the irradiated bodies, wherein each of the plurality of first irradiation holes is corresponding to one of the accommodating chambers, the radioactive rays generated by the radioactive source irradiate the corresponding one of the irradiated bodies in each of the accommodating chambers through a corresponding one of the first irradiation holes, and a maximum distance from inner walls of the first irradiation holes to the first central axis is smaller than a minimum distance from an inner wall of the beam outlet to the first central axis.

14. The animal irradiation system according to claim 1, wherein the box body comprises a base and a cover plate, the base comprises a bottom plate and separators, the separators are a plurality of protruding parts extending from the bottom plate or the cover plate along directions parallel to the second central axis and distributed circumferentially around the second central axis, and the box body is circumferentially divided into the plurality of the accommodating chambers by the separators around the second central axis.

15. The animal irradiation system according to claim 14, wherein the first irradiation holes are circumferentially distributed around the second central axis and provided on one of the bottom plate and the cover plate, and the first irradiation holes extend through in a direction parallel to the second central axis to communicate with each of the accommodating chambers.

16. The animal irradiation system according to claim 15, wherein the other one of the bottom plate and the cover plate is provided with vent holes penetrating in directions parallel to the second central axis.

\* \* \* \* \*